United States Patent [19]

Katz et al.

[11] Patent Number: 4,767,873
[45] Date of Patent: Aug. 30, 1988

[54] HELICAL METALLOCENE OLIGOMERS AND A METHOD FOR THEIR PREPARATION

[75] Inventors: Thomas J. Katz, New York, N.Y.; Anantha Sudhakar, Madison, Wis.

[73] Assignee: The Trustees of Columbia University in the City of New York, New York, N.Y.

[21] Appl. No.: 905,930

[22] Filed: Sep. 10, 1986

Related U.S. Application Data

[63] Continuation-in-part of Ser. No. 775,761, Sep. 13, 1985, abandoned.

[51] Int. Cl.⁴ .................... C07F 15/06; C07F 15/00; C07F 13/00; C07F 11/00
[52] U.S. Cl. ......................... 556/42; 556/46; 556/52; 556/53; 556/60; 556/112; 556/121; 556/129; 556/143; 556/144; 556/443; 534/10; 534/11; 585/26; 585/27; 204/157.92; 204/157.73; 204/157.74; 204/157.94
[58] Field of Search .................... 556/42, 46, 52, 53, 556/60, 129, 112, 121, 143, 144, 443; 534/10, 11; 585/26, 27; 204/157.92, 157.73, 157.74, 157.94

[56] References Cited

U.S. PATENT DOCUMENTS

2,414,118  1/1947  Orchin .
3,000,984  9/1961  Halleux .
3,350,369  10/1967  Rosenberg et al. .
3,711,567  1/1973  Innes .
4,166,181  8/1979  Dokunikhin et al. .

OTHER PUBLICATIONS

Katz et al, JACS, 101(15), pp. 4259–4267 (1979).
Sudhakar et al, JACS, 108(1), pp. 179–181 (1986).
Chemical Abstracts, 97, 6474g (1982).

*Primary Examiner*—Paul F. Shaver
*Attorney, Agent, or Firm*—John P. White

[57] ABSTRACT

The invention describes a helicene compound having the structure

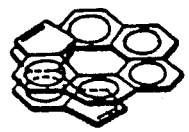

which contains seven six-membered conjugated aromatic rings capped by two five-membered rings which do not superimpose on each other.

The invention also describes a helical metallocene oligomer capped by unsaturated five-membered rings, having the structure:

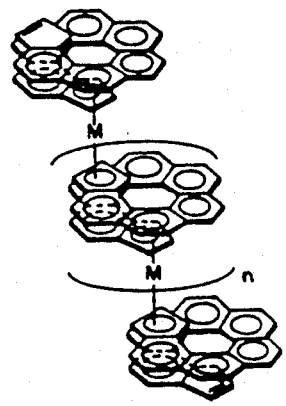

wherein M is a transition metal halide and n=1 to 100.

Method for the preparation of these compounds are also presented.

19 Claims, 7 Drawing Sheets

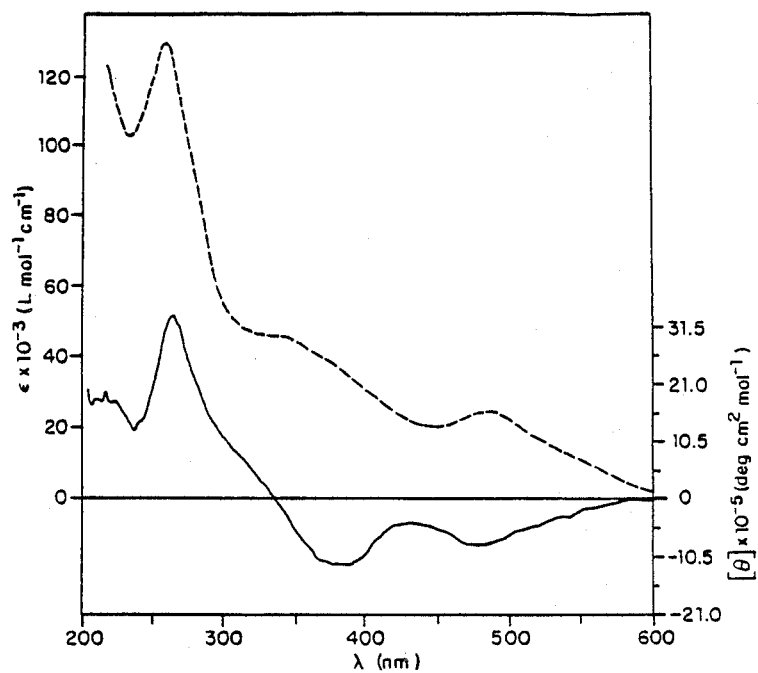

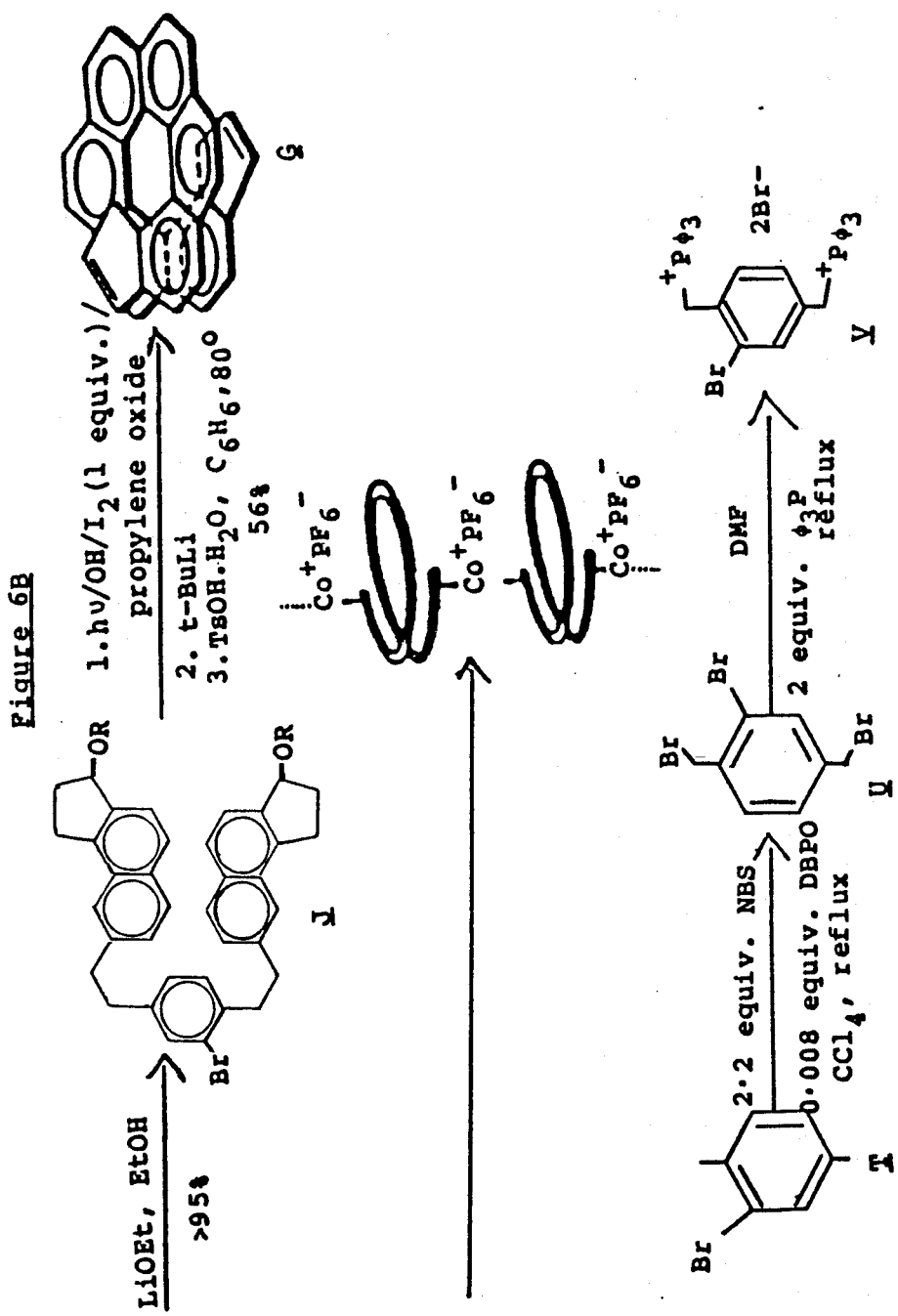

HELICAL METALLOCENE OLIGOMERS AND A METHOD FOR THEIR PREPARATION

BACKGROUND OF THE INVENTION

The invention described herein was made in the course of work under Grant No. DMR-82-13794 from the National Science Foundation. The U.S. Government has certain rights in this invention.

This application is a continuation-in-part of U.S. Ser. No. 775,761, filed Sept. 13, 1985, now abandoned, the contents of which are hereby incorporated by reference into the present application.

Throughout this application various publications are referenced by arabic numerals within parentheses. Full citations for these references may be found at the end of the specification immediately preceding the claims. The disclosures of these publications in their entireties are hereby incorporated by reference into this application in order to more fully describe the state of the art as known to those skilled therein as of the date of the invention described and claimed herein.

Attempts have been made in the past to synthesize polymers like A, in which conjugated arrays and metal atoms alternate. One such attempt resulted in the formation of compounds in which the bonds created in the polymerization process were between carbon atoms and when applied to preparations of polyferrocenylenes (structure B) gave small oligomers that were well characterized (14) and larger polymers that were sometimes impure (15, 16).

In other experiments, the carbon-metal bonds were created in the polymerization process, and when applied to reactions of transition metal salts with dilithium asindacenide (C) gave $(C_{12}H_8M)_n$, where M is Fe, Co, or Ni; with dilithium pentalenide (D) $(C_8H_6M)_n$ (here M=CO or Ni), and with dilithium fulvenide (E) $(C_{10}H_8M)_n$, where M=Fe, Co, Ni or Mo. However, the value of n in each of these experiments was 2, i.e. the products were only dimers.

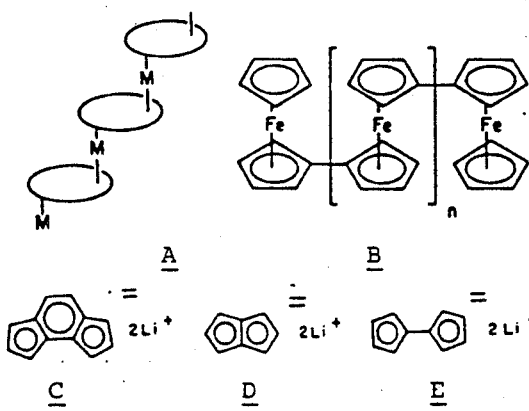

A hypothesis for avoiding dimerization was presented. This idea involved incorporating the hydrocarbon sandwiches of the dimers within helicenes. Conjugated helical hydrocarbon dianions capped by five-membered rings were synthesized for the purpose. It was suggested that reacting these aromatic anions with transition-metal halides would produce metallocene polymers. However, the aromatic dianions produced were too small to give polymers.

Dimers can form only when the number of extending benzene rings is few. Monomeric metallocenes (structure F where M=Fe, $Co^+PF_6^-$) are formed when the five-membered rings superimpose overlapping unsaturated five-membered rings which can yield polymeric metallocenes.

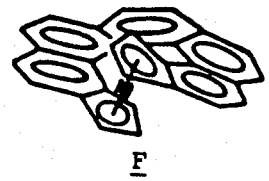

F

BRIEF DESCRIPTION OF THE FIGURES

FIG. 5 depicts the CD (solid line, $5 \times 10^{-6}M$) and UV (broken line, $5 \times 10^{-6}M$) spectra of the oligomer having structure H (M=$Co^+PF_6^-$) in $CH_3CN$. UV peaks (log $\epsilon$) are at 486 (4.41), 340 (4.66), and 258 nm (5.11). CD peaks ($[\theta]$) are at 263 ($3.30 \times 10^6$), 382 ($-1.19 \times 10^6$), and 474 nm ($-8.40 \times 10^5$).

SUMMARY OF THE INVENTION

Figure 1:
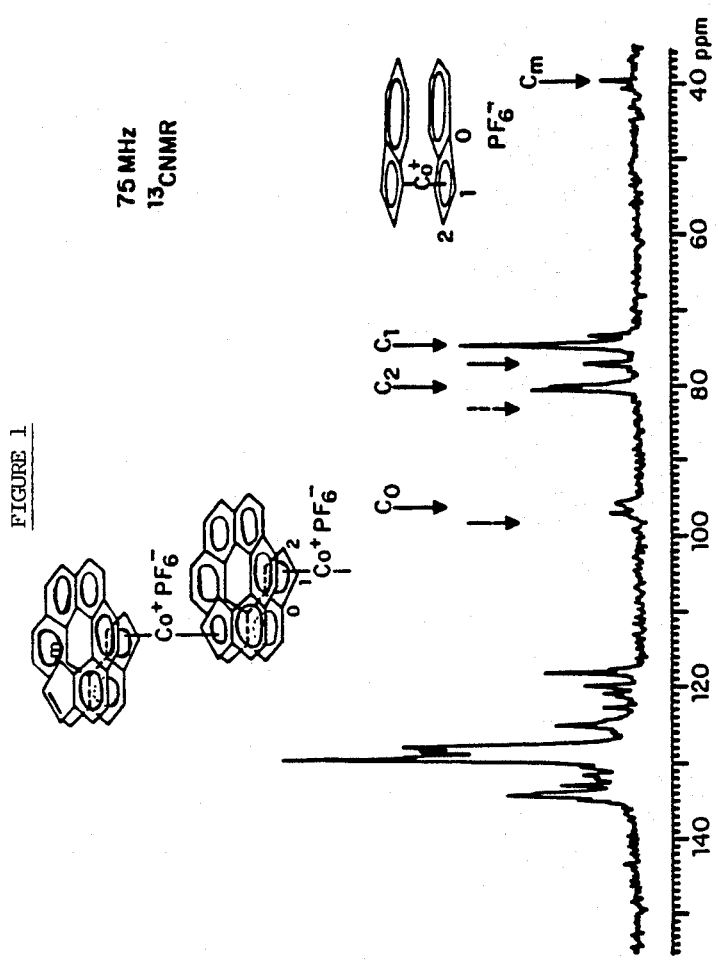
FIG. 1 depicts the 75 MHz $^{13}C$ NMR spectrum of the oligomer having structure H in $CD_3COCD_3$. The spectrum, measured using 90° pulses and no relaxation delay, is displayed with 5 Hz line broadening. The chemical shifts were measured assuming that of $CD_3COCD_3$ to be 29.8 ppm. Peaks assigned to metallocene carbons are pointed out, and the dotted arrows show where the corresponding resonances appear for the indene analogue (pictured). The peak marked $C_m$ is attributed to the methylene carbon (labeled on the diagram).
Figure 2:
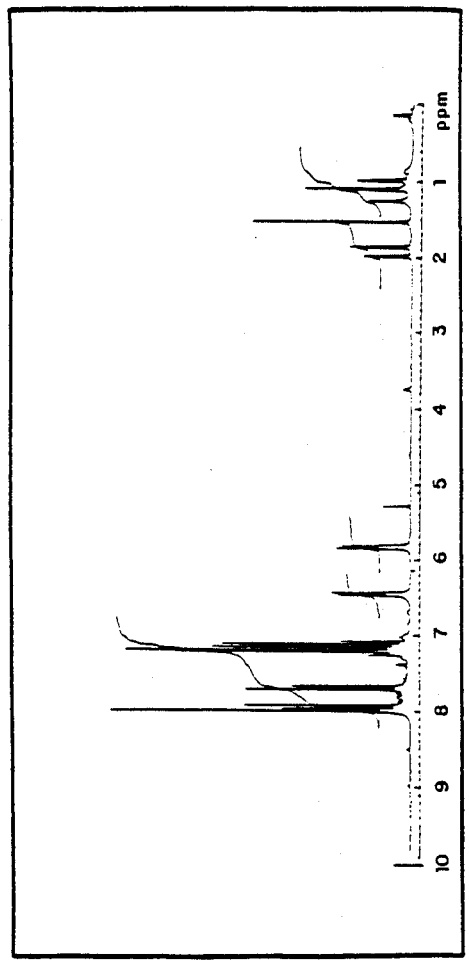
FIG. 2 depicts the 200 MHz $^1H$ NMR spectrum of the helicene having structure G in $CDCl_3$.
Figure 3:
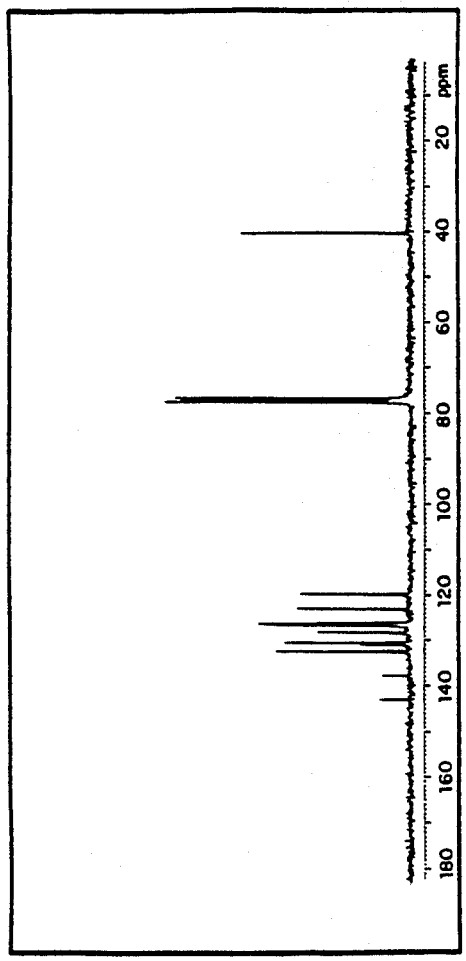
FIG. 3 depicts the $^{13}C$ NMR spectrum of the helicene having structure G in $CDCl_3$. The resonances of carbons of the five-membered ring are assigned to peaks at 40.2, 130.5, 132.4, 137.7 and 142.9 ppm (see reference). The seven protonated benzenoid carbons are assigned to peaks at 119.6, 122.9, 126.0, 126.3, 126.4, 126.5, and 128.1 ppm. Five of the six quaternary benzenoid resonances are visible: 126.2, 128.5, 130.3, 130.9, and 132.3 ppm.
Figure 4:
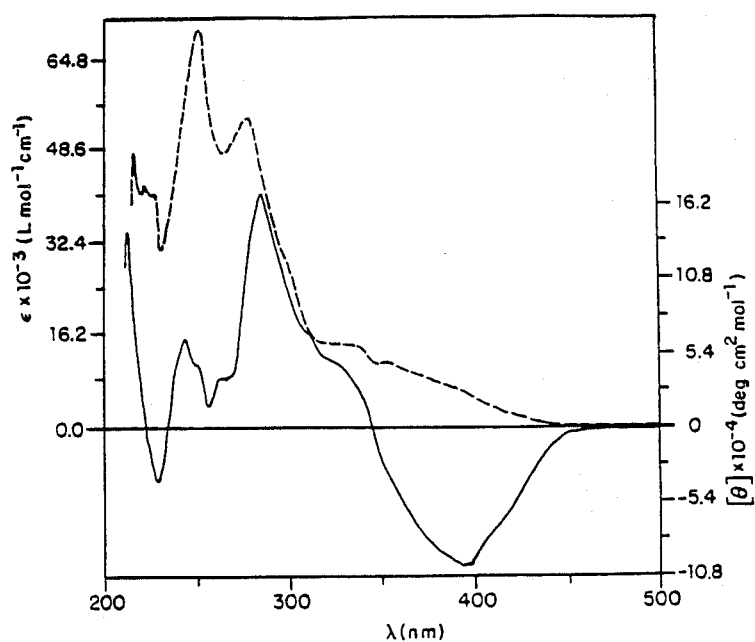
FIG. 4 depicts the CD (solid line) an UV (broken line) spectral of the helicene having structure G ($6.17 \times 10^{-6}M$) in $CH_3OH$. UV peaks (log $\epsilon$) are at 354 (4.05), 336 (4.16), 278 (4.73), and 252 nm (4.84). CD peaks ($[\theta]$) are at 243 ($6.48 \times 10^4$), 285 ($1.75 \times 10^5$), and 395 nm ($-1.0 \times 10^5$).

The present invention concerns a helicene compound having the structure:

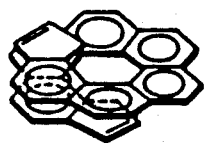

G which contains seven six-membered conjugated aromatic rings capped by two five-membered rings which do not superimpose on each other.

The present invention also concerns a helical metallocene oligomer capped by unsaturated five-membered rings, having the structure:

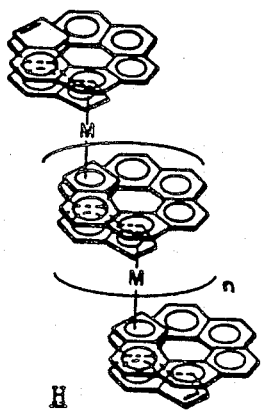

wherein M is a transition metal halide and n=1 to 100.

A method of preparing the helicene is provided which comprises:

(a) contacting a compound having the structure:

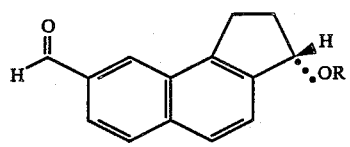

wherein R=(t-Bu)Me$_2$Si, with 1,4-bis[(C$_6$H$_5$)$_3$P+CH$_2$]-2-Br—C$_6$H$_3$, under suitable conditions to form a compound having the structure:

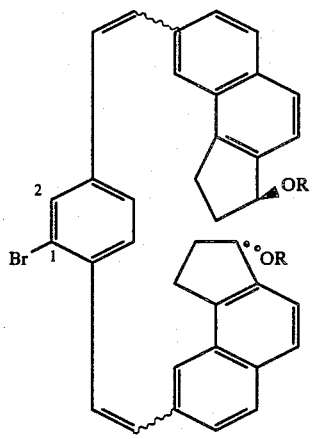

(b) then, subjecting the compound formed in step (a) to light energy in the presence of an acid scavenger compound which results in a photocyclization; and
(c) finally, contacting the cyclized product of step (b) with a suitable reducing agent and an acid to form the helicene.

A method of preparing the helical metallocene oligomer is also provided which comprises:
(a) first, contacting the helicene prepared as described above with a suitable base;
(b) contacting the product resulting from step (a) with a transition metal halide in a suitable solvent;
(c) contacting the product of step (b) with a suitable oxidizing agent; and
(d) contacting the product of step (c) with a hexahalophosphate salt to produce the helical metallocene oligomer.

DETAILED DESCRIPTION OF THE INVENTION

The present invention is a new composition of matter, a polymer comprised of alternating metal atoms and rings of atoms in which the path of conjugation of so-called $\pi$-electrons extending from one metal to the next is unbroken either by atoms that do not have available a single $\eta$-electron to continue the path of conjugation or in which the carbon skeleton does not constrain the $\pi$-electrons on adjacent atoms to almost parallel orbitals. The $\pi$-electrons are those valence shell electrons on the skeletal atoms in excess of the one required to bond to each adjacent atom. The invention includes those examples of materials in which the skeleton is coiled in a helix, and those examples in which one of the two directions predominate in which the helices wind. It includes examples of the materials described in the first sentence above that are optically active.

It is contemplated that the metals useful in the present invention are any metals chosen from among the transition elements (i.e. groups 3–10 of the most recent revision of Mendeleev's Table of the Elements), the lanthanides or the actinides.

An example of the present invention is the polymeric cobaltocinium hexafluorophosphate shown below.

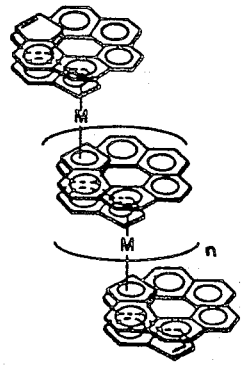

Foreseeable uses of the materials of the present invention include those exploiting the electrical, magnetic, and optical properties of the materials and their derivatives. The metallocenes of the present invention may also be the basis for new catalysts that induce high asymmetry in chemical transformations.

Scheme I

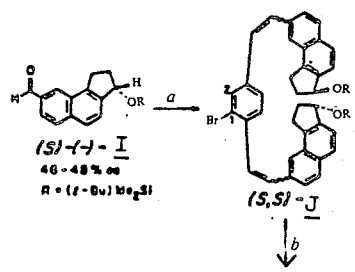

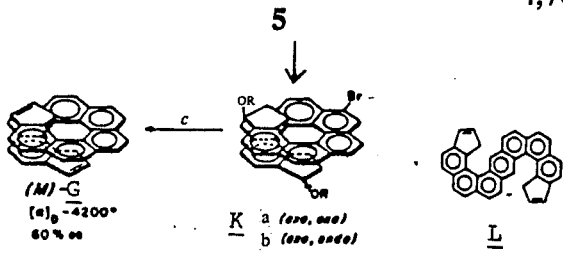

$^a$1,4-bis[(C$_6$H$_5$)$_3$P$^+$CH$_2$]-2-Br—C$_6$H$_3$, 2Br$^-$ (0.5 equiv wt), LiOEt (1.1 equiv wt), EtOH, 25° C., 5–12 h, 95–100% yield). $^b$h, C$_6$H$_6$, I$_2$ (2.2 equiv wt), propylene oxide, 4–12 h. $^c$(1) t-BuLi, tetrahydrofuran, 78° C.; (2) H$_2$O; (3) p-toluenesulfonic acid, C$_6$H$_6$, 80° C., 10 min (45–65% yield from J).

The preparation of hydrocarbon G, summarized in Scheme I, is easy to carry out (7). The phosphonium salt of step a was prepared from 2-bromo-p-xylene (2.2 equiv. N-bromosuccinimide, 0.008 equiv. dibenzoylperoxide, CCl$_4$, reflux, 3h, 75% yield, then 2 equiv. triphenylphosphine in DMF, 91% yield. All new compounds exhibited satisfactory NMR, IR, and (except for the salts), mass spectra (including, for key compounds, high resolution mass spectra). In the $^1$H NMR spectrum of G, as in other helicenes, the olefinic and allylic proton resonances are shifted to higher field than in simpler indenes (1, 3b, 7). The isomers of J in which both ether functions are in the other benzylic position do not give appreciable amounts of helical product, and the one in which the ethers are in the non-benzylic position gives a helical product from which the ethers cannot be eliminated (7).

The method of preparation has three main features. (1) A bromine directs the photocyclization to give the helix by blocking both the position it occupies (C-1) and the position adjacent (C-2) (5). This atom is then easy to remove. In its absence, the cyclization gives only the planar isomer L and none of the helicene G. Resonances characteristic of G are absent in the $^1$H NMR spectrum of the crude product (7). Propylene oxide is required during the photocyclization to consume the HI generated, thereby preventing the ROH functions from being eliminated prior to cyclization (7). In the absence of propylene oxide, photo-cyclization of (R,R)-K gives helical product, but in a racemic form (7). The direction in which the helix winds is that expected if silyloxyls outside the helix are favored. The helicity is thus controlled by the stereochemistry of I (7).

J is prepared from (R)-I [46–52% enantiomeric excess (ee)] and irradiated in the presence of traces of iodine, it gives helical bis-indene (containing the bromine) whose [α]$_D$ (+82°) corresponds to ca. 1% ee. The double bonds in this material are shifted from their position in G (7).

For the absolute configuration of (S)-(−)-I see ref. 7. The absolute configuration of G was assigned on the assumption that, like all helicenes, the (M)-enantiomer is levorotatory at 578 nm and exhibits a negative Cotton effect in its CD spectrum in methanol for the band at 395 nm ([α]=−1×10$^5$ deg cm$^2$ mol$^{-1}$) (7). Its ee was measured by analyzing the $^1$H NMR resonances of one of its CH$_2$'s when a solution (2.5 mg) in CDCl$_3$ (1 mL) contained Ag(fod) (4 mg) and Eu (hfc)$_3$ (12 mg) (7). The rotation of a sample, [α]$_D$=4200°, measured to have an ee of 60% implies that [α]$_D^{max}$=7000°.

Structure (S,S)-J is contacted, e.g. mixed in a suitable solvent, contacted with a suitable reducing agent (e.g. t-BuLi) which eliminates the bromine group and then contacted with an acid (e.g. p-toluene sulfonic acid) which eliminates the RO-groups and introduces two double bonds. (S,S)-J of Scheme I gives 27% structure Ka (recognized by the symmetry of the $^1$H NMR after debromination), 12% Kb, and no detectable ($^1$H NMR) endo, endo isomer. The latter could not have been misassigned the exo, exo-structure since the (M)-configuration requires more asymmetric carbons to have the (R)-stereochemistry than are present in J (7).

When the helicene G is combined first with t-butyllithium and then with CoBr$_2$.DME (DME=1,2-dimethoxyethane) and the product is oxidized in aqueous HCl with FeCl$_3$, added NH$_4$PF$_6$ precipitates a red cobaltocinium salt (69% yield after washing with water and ether, and drying) that elemental and spectroscopic analyses indicate to be an oligomer of structure H (M-Co$^+$PF$_6$) (7, 8). The anion of the salt of the hexafluorophosphate (PF$^-$$_6$) substitutes for the bromines of CoBr$_2$. This material is soluble in acetone and acetonitrile, and was purified by adding its solutions in acetone to vigorously stirred ether, then filtering and drying the resulting precipitate. It is unaffected by heating in air at 260° C.

Evidence that the cobaltocinium salt is a short polymer of structure H is the following. The $^{13}$C NMR spectrum (FIG. 1) consists of resonances at positions characteristic only of benzenoid helicenes (including G) (135–118 ppm), (10) of bis(indenyl)cobalt(III) salts (80–74 ppm), (11) and of the methylene group of G (40 ppm, this last peak very small, corresponding to approximately two end groups for every 3–4 cobalts) (11). FIG. 1 marks (with dotted arrows) the positions at which the carbon atoms of the five-membered rings of bis(indenyl)cobalt(III) hexafluorophosphate exhibit their resonances, and it shows that the corresponding peaks attributed to structure H are all 2 ppm to their right. This shift is expected, for when comparing the resonances of carbon-2 in [4]- and [7]-helicenes, (the second protonated carbon on the first ring counting from the inside of the helix) the latter (in which this carbon is above another ring) is shifted to higher field by 2 ppm (10). Another significant feature of the spectra is the absence of resonances around 51.3 ppm, characteristic of 1,1'-bi-$^1$H-indene ["bi(3-indenyl)"], showing that the transition metal ions do not couple the carbanions by oxidation.

The elemental analysis corresponds to a composition of 3.13 hydrocarbons, 2.13 CoPF$_6$'s, and 3.45±1.4 H$_2$O's. The molecular weight is thus ca. 1.9×10$^3$. Three independently prepared samples were analyzed. Anal. calcd. for 2.0 H$_2$O's: C, 71.65; H, 3.66; Co, 6.65. Found: C, 71.24; H, 3.90; Co, 6.71. Anal calcd. for 4.9 H$_2$O's: C, 69.93; H, 3.88; Co, 6.49. Found: C, 69.82; H, 3.73; Co, 6.48. The third sample's analysis corresponded to that of a slightly larger molecule. Anal. calcd. for 3.49 rings, 2.49 CoPF$_6$'s, 7.3 H$_2$O's: C, 67.96; H, 3.92; Co, 6.61; F, 12.78. Found: C, 68.18; H, 3.61; Co, 6.63; F, 12.45. For a simple complex of 2 rings and 1 Co, calcd. is C, 77.84; H, 3.81; Co, 5.30; and for an infinite polymer, C, 65.89; H, 3.07; Co, 8.97.

The optical activity is very high, 4.1 (±0.6) times as great as that of G. When measured using a sample prepared from G whose enantiomeric excess (ee) was 60%, [α]$_D$ for cobaltocinium salt of 100% ee is 26,000. The molar ellipticities of the CD peaks at 474 and 263 nm (−8.4×10$^5$ and −3.3×10$^6$, assuming the molecular weight to be 1.9×10$^3$) are 7.2 and 6.0 times as large as for the corresponding peaks in F (M=Co$^+$$^{PF}$$_6$$^-$) (7).

Figure 6A:
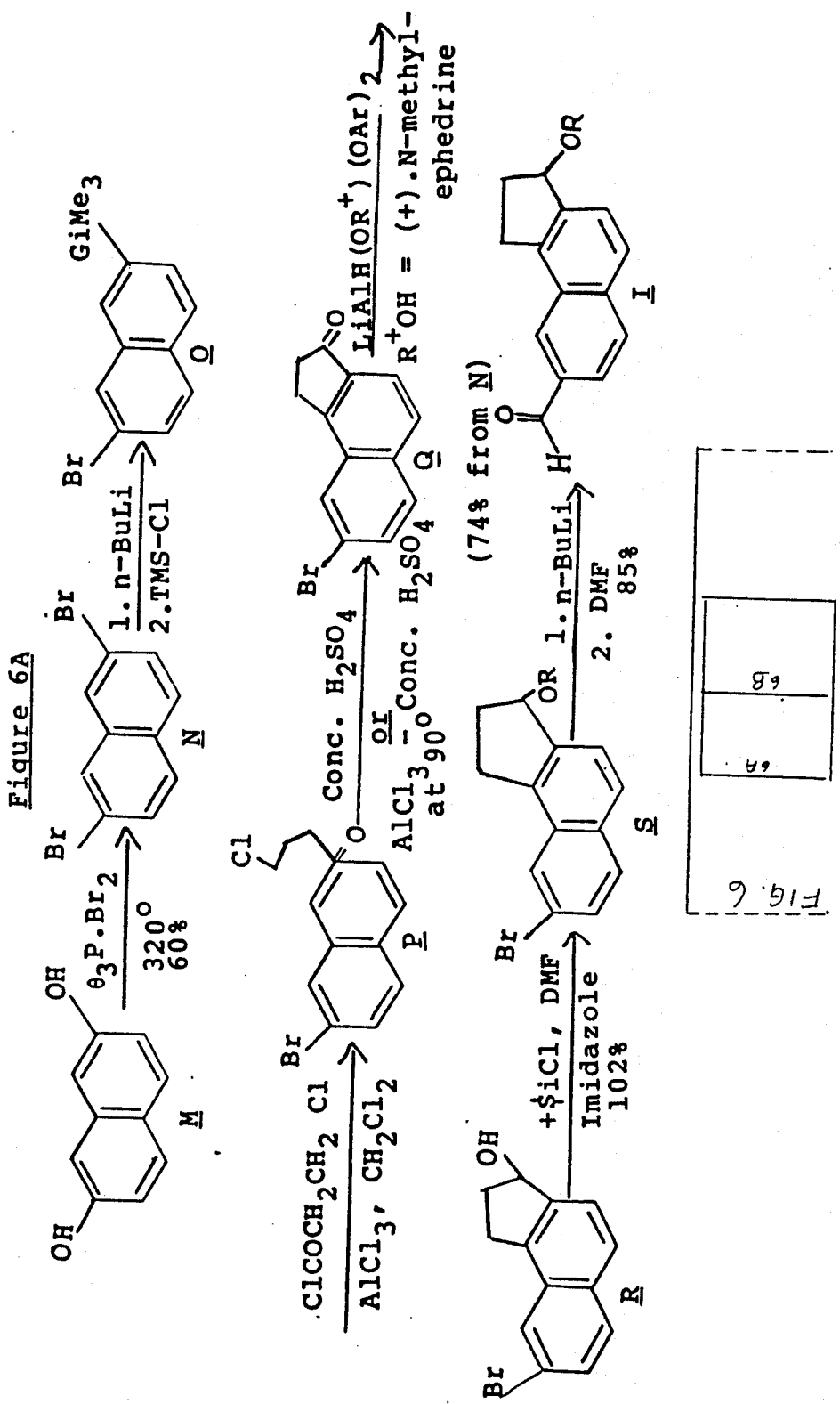
FIGS. 6A and B depicts the chemical reaction and products of each step described in Examples 1-11.

The present invention is further illustrated by reference to the examples which follow. These examples are keyed to the reactions and structures depicted in FIG. 6.

EXAMPLE 1

In an oven-dried 2 L 3-necked round-bottomed flask, fitted with a mechanical stirrer, an argon inlet and a 250 mL dropping funnel, was placed 114.4 g (0.4 mol) 2,7-dibromonaphthalene (FIG. 6, Structure N) and 1 L freshly distilled THF. The solution was stirred and cooled to $-78°$ under argon. A solution of n-butyllithium (175 mL 2.4M, 0.42 mol) in hexanes was injected into the addition funnel and added in drops in 30 min. The greenish-yellow mixture was stirred at $-78°$ C. for another 20 min. Dry chlorotrimethylsilane (81 mL, 69.5 g, 0.64 mol, distilled from $CaH_2$) was then added in 10 min from the dropping funnel, resulting in an exothermic reaction and a color change to orange. After the exotherm subsided (ca. 15 min), the cooling bath was removed and the mixture was allowed to warm to room temperature and stirred for 2 h. Solvent was evaporated to about 250 mL and the mixture was diluted with 1 L of water. It was then extracted with ether ($1 \times 600$ mL, $3 \times 100$ mL ether). The combined ether extracts were washed with 200 mL brine, dried over anhydrous magnesium sulfate, and filtered. Evaporating the solvent gave 126 g (112%) yellow-orange liquid, which when kept at $15°$ C. overnight solified to a pale yellow mass. This crude product is pure enough for the next step, although the results of that step imply that 2-bromonaphthalene is present as an impurity.

$^1$H NMR (200 MHz, $CDCl_3$): $\delta 7.99$ (dd, J=1.5, 0.8 Hz, 1.01H), 7.88 (d, J=0.8 Hz, 0.96H), 7.77 (d, J=8.1, 1.2 Hz), 7.67 (d, J=8.7 Hz), 7.58 (dd, J=8.1, 1.2 Hz), 7.52 (dd, J=8.7, 2.0 Hz)—the integral of 7.77–7.52 corresponds to 4.4H—0.32 (s, 8.6H).

EXAMPLE 2

Anhydrous aluminum chloride (70 g, 0.526 mol, Fisher) was placed in a 1 L 3-necked flask fitted with a mechanical stirrer, nitrogen inlet, and 250 mL addition funnel. Dichloromethane (100 mL) and a solution of 61 g (0.48 mol) 3-chloropropionyl chloride in 50 mL dichloromethane were added to the flask while its contents were stirred. The flask was cooled in dry-ice acetone, and a solution of 126 g bromosilane (FIG. 6 structure Q) in 200 mL dichloromethane was added in 35 min. The mixture was stirred for 10 min at $-78°$ C. and allowed to warm to room temperature during 45 min. The reaction mixture was poured into ca. 1000 mL ice containing 100 mL conc. hydrochloric acid. The mixture was extracted with 1.5 L dichloromethane, and the aqueous layer was extracted with additional dichloromethane ($3 \times 200$ mL). The combined organic layers were washed once with 1.5 L water, dried ($MgSO_4$), filtered, and evaporated to give 135 g crude structure P as an off-white solid. This was cyclized without further purfication. However, it could be purified by shaking with 500 mL petroleum ether and filtering. The precipitate was then pure structure P (90 g, 76%), and the filtrate on evaporation gave 44 g of dark liquid containing some structure P.

For the pure material the m.p. is $120°$ C. and the $^1$H NMR (200 MHz, $CDCl_3$): $\delta$: 8.35 (br s, 0.79H), 8.12 (d, J=0.95 Hz, 0.79H), 8.02 (dd, J=8.6, 1.7 Hz, 1.11H), 7.87 (d, J=8.6 Hz, 1.05H), 7.75 (d, J=8.9, 1.05H), 7.66 (dd, J=8.8, 1.8z, 1.05H), 3.96 (t, J=6.9 Hz, 2.10H), 3.56 (t, 6.9 Hz, 2.10H).

EXAMPLE 3

Method A: Anhydrous $AlCl_3$ (35 g, Fisher) was weighed into an oven-dried 2 L 3-necked flask fitted with a mechanical stirrer, a drying tube the outlet of which is vented to the hood, and a stopper. Concentrated sulfuric acid (325 mL, Mallinckrodt, Electronic grade) was added, and the mixture was stirred in an ice-water bath. Crude structure P (65 g) was added to the suspension in small portions in 20 min while stirring vigorously. The reaction mixture became yellow and then orange. The stopper was replaced in a thermometer and the flask was heated by means of a mantle. When the internal temperature was $65°$ C., the stirring rate was increased, and rate of heating decreased to control the foaming. After the foaming had subsided, the mixture was held at $98°$ C. for 1 h. It was then cooled to ca. $70°$ C., and cautiously poured into 4 L of ice-water containing ice. The mixture was stirred for 2 h and extracted with $CH_2Cl_2$ and filtered through a $6'' \times 5$ cm column of neutral alumina, eluting with $CH_2Cl_2$. The filtrate was evaporated, giving 38.7 g (68% from P, 76% from N) O as a pale yellow solid, m.p. $131°-132°$ (lit. $132°-134°$ C.) (3b). The 200 MHz $^1$H NMR is identical with that of a sample prepared according to the previously published procedure (3b). The IR spectrum also was identical to that reported for structure O (3b). Purification of crude O may also be achieved by crystallization as shown below.

Method B: 89.5 g of purified P was added over 40 min to 300 mL concentrated sulfuric acid in a 2 L 3-necked flask (the apparatus was the same as in method A above). The reaction mixture was heated to $90°$ C. (internal temperature) and maintained at this temperature for 80 min. After cooling, the reaction mixture was poured into ice-water, extracted with $CH_2Cl_2$ ($15 \times 200$ mL), the organic layer washed with 2 L water, dried ($MgSO_4$), filtered and evaporated. The residue was crystallized from $CH_2Cl_2$-ether, giving 61 g off-white solid. A second crop of O, 15 g was obtained after chromatography of the mother liquor. The total yield of O, 76 g, represents a 73% yield from 2,7-dibromonaphthalene.

EXAMPLE 4

Lithium aluminum hydride (8.05 g, 0.2 mol, Aldrich) and dry ether (100 mL) were placed in a 2 L 3-necked flask fitted with mechanical stirrer, 250 mL Kontes addition funnel and a dry condenser carrying a $N_2$ inlet. To the stirred suspension was added during 20 min a solution of 35.8 g (0.2 mol) (+)-N-methylephedrine in 350 mL dry ether. The reaction mixture was refluxed for 1 h, cooled, and a solution of 48.9 g (0.4 mol) 3,5-dimethylphenol (Aldrich) in 220 mL dry ether was added over a period of 225 min. The mixture was again refluxed for 1 h, cooled in ice-salt-water mixture (internal temp. $0°$ C.), and 20.g O was added in one portion. The mixture was stirred overnight.

Water (10 mL) was added in drops to the reaction mixture, followed by 400 mL 1M hydrochloric acid. After 5 min, the ether layer was separated and the aqueous layer extracted with 200 mL ether. The combined ether layer was washed with 1M HCl ($1 \times 300$ mL), water ($1 \times 200$ mL), 10% NaOH solution ($3 \times 200$ mL), brine ($1 \times 500$ mL), and dried over $MgSO_4$. The solvent was then evaporated to a small volume, and the solid was filtered giving 11.5 g R, $[\alpha]_{578}^{20} = -43°$ (c=0.40, CH$_2$Cl$_2$). A second crop (4.1 g, $[\alpha]_{578}^{20} = -0.56°$ (c=0.36, CH$_2$Cl$_2$) was obtained from the filtrate when pentane was added. Evaporation gave a third portion, 4.3 g $[\alpha]_{576}^{20} = -9.2°$. The NMR spectrum of R was identical to that of its racemate (3b). The results of two related experiments are these:

(1) from 32.6 g ketone there were obtained 23.4 g R with $[\alpha]_{578} = -40°$, 4.3 g R with $[\alpha]_{578} = -2°$, and 4.8 g R with $[\alpha]_{578} = -12.4°$; (2) from 32.6 g ketone, 24.3 g R with $[\alpha]_{578} = -41.2°$ (ee=46%) and 10.2 g R with $[\alpha]_{578} = -6.67°$.

The NMR spectra of the O-methylmandelate ester (12) and the CD spectrum of the p-bromobenzoate ester (13) show that the (−)-enantiomer has the (S)-configuration.

EXAMPLE 5

S-(−)-R (34.9 g, 0.133 mol), $[\alpha]_{578}^{20} = -41°$ (c=0.4, CH$_2$Cl$_2$), was mixed with 30 g (0.199 mol) t-butyldimethylsilylchloride (Petrarch Systems) and 28 g (0.412 mol) imidazole (Aldrich) in 400 mL DMF (Fisher, spectroscopic grade). The solution was stirred at room temperature under N$_2$ for 200 min, diluted with 800 mL ether, and shaken with 2 L cold water. The ether layer was washed with brine (2×500 mL), dried (MgSO$_4$), filtered and evaporated, giving an orange oil that eventually solidified. This was chromatographed on a silica (6"×10 cm dia.) column, eluting with CH$_2$Cl$_2$-petroleum ether (1:7). The product eluted quickly, and evaporation gave 51 g (102%) white solid, $[\alpha]_{578}^{20} = -50°$ (c=0.2, CH$_2$Cl$_2$). The NMR spectrum of this material was identical to that reported for racemic S (3b).

EXAMPLE 6

S-(−)-S (34.2 g, 0.091 mol, $[\alpha]_{578} = -50°$) was dissolved in 1 L dry THF and 0.5 L dry ether in a 2 L 3-necked flask fitted with an Ar inlet, low-temperature thermometer and a septum. The solution was cooled to −78° C. under argon and 80 mL (0.208 mol) of 2.6M n-butyllithium in hexanes was injected through the septum during 5 min. The slightly greenish solution was stirred at −78° C. for 20 min, and then 100 mL dry DMF (distilled from BaO under reduced pressure) was injected. The cooling bath was removed and the solution stirred for 70 min. Quenching with 200 mL water, extraction with 700 mL ether, washing with brine (1 L, 2×0.5 L, re-extracting with 2×400 mL ether) and again with brine (400 mL), drying (MgSO$_4$), and evaporation gave an oil, which was chromatographed on silica. CH$_2$Cl$_2$-petroleum ether (1:2) eluted an impurity, and CH$_2$Cl$_2$-petroleum ether (1:1 to 2:1) eluted the aldehyde I, 25.2 g (85%) as a pale yellow solid, $[\alpha]_{578}^{20} = -42.7°$ (c=0.3, CH$_2$Cl$_2$). The NMR spectrum of this material was identical to that of racemic I (3b).

EXAMPLE 7

2-Bromo-p-xylene T (46.25 g, 0.25 mol, Aldrich) was mixed with 98 g (0.55 mol) N-bromosuccinimide (Fisher) and 500 mL carbon tetrachloride in a 1 L round-bottomed flask. Dibenzoyl peroxide (500 mg) was added, and the mixture was refluxed for 100 min, cooled, filtered, and the filtrate was evaporated to a small volume. Trituration with pentane gave a precipitate, which was filtered giving 18.5 g white solid, m.p. 86° C. A second crop (20.5 g) was obtained from the mother liquor. The total yield of U was 39.0 g (45.5%).

$^1$H NMR (270 MHz, CDCl$_3$) δ: 7.60 (d, J=2 Hz, 1H), 7.42 (d, J=7.9 Hz, 1H), 7.31 (dd, J=7.9 Hz, 2 Hz, 1H, 4.57 (s, 2H), 4.40 (s, 2H).

EXAMPLE 8

The tribromide U (39 g) and 63 g triphenylphosphine were dissolved in 300 mL dry DMF, and the solution was refluxed for 3 h. After cooling, 200 mL ether was added, and the precipitate was filtered. The solid was washed with ether to give V as a white fluffy solid, m.p. 260° C. Yield 89.2 g (91%).

$^H$ NMR (300 MHz, CD$_3$CN) δ: 7.9–7.8 (m, 6H, 7.7–7.45 (m, 24H), 7.09 (br s, 1H), 7.0–6.95 (dd, J=8.0, 2.4, 1H), 6.9–6.85 (br d, J=8.08), 4.85 (dd, 4H).

EXAMPLE 9 n-Butyllithium (37 mL, 2.4M, 88.8 mmol) was injected into a 2 L 3-necked flask fitted with argon inlet, mechanical stirrer, and an addition funnel. The flask was cooled to −78° C., and 400 mL 200-proof ethanol was added in drops from the funnel during 20 min. The solution was then allowed to warm to room temperature.

The bis(phosphonium) bromide V (35, 0.040 mol) and S-(−)-aldehyde I-(25.2 g, 0.077 mol) were suspended in 500 mL 200-proof ethanol in a 2 L 3-necked flask fitted with an Ar inlet, mechanical stirrer, and a septum. During 30 min the lithium ethoxide solution prepared above was transferred to the solution via a cannula. The resulting yellow solution was stirred overnight, during which a fine yellow precipitate appeared. The suspension was poured into 2 L water, and the mixture was extracted with CH$_2$Cl$_2$ (1×600 mL, 2×300 mL). The CH$_2$Cl$_2$ extract was washed with 1 L brine, dried (MgSO$_4$), and evaporated. The yellow oily residue was chromatographed on silica, eluting with CH$_2$Cl$_2$-petroleum ether (1:5 to 1:4), giving 31.3 g (100% yield) of yellow solid, $[\alpha]_{578}^{20} = -67.8°$ (c=0.39, C$_6$H$_6$).

$^1$H NMR (200 MHz, CDCl$_3$): δ: 8.0–6.5 (m, 19.4H), 5.45 (br dd, 2.16H), 3.6–2.8 (m, 3.69H), 2.8–2.5 (m, 1.84H), 2.3–1.9 (m, 1.90H), 1.1–0.9 (3 singlets, 16.5H), 0.3–0.15 (m, 10.3H).

IR (KBr, cm$^{-1}$): 2955, 2928, 2889, 2855, 1420, 1461, 1360, 1252, 1105, 1051, 1037, 985, 955, 884, 861, 836, 775.

EXAMPLE 10

(S,S)-(−)-J (200 mg) and 150 mg iodine dissolved in 440 mL benzene (Fisher, spectra-analyzed) was degassed with argon for 20 min and 5 mL propylene oxide was added. The solution was then irradiated for 12 h through a water-cooled pyrex jacket by means of a Hanovia medium pressure Hg lamp. The solvent was evaporated. This experiment was repeated ten times, and the combined residues, dissolved in CH$_2$Cl$_2$-petroleum ether (1:1), were filtered through a 4" column of neutral alumina. Evaporation gave an orange solid, which was taken up in 100 mL dry THF in a 250 mL round-bottomed flask and cooled to −78° C. under Ar. t-Butyllithium in pentane (10 mL, 1.7M) was added, and after the dark mixture had stirred at −78° C. for 20 min, it was quenched with water and allowed to warm to room temperature. Extraction into 100 mL ether, washing with brine, drying (MgSO$_4$), and evaporation gave a yellow-orange solid, which was dissolved in benzene (100 mL) containing p-toluenesulfonic acid monohydrate (50 mg). The solution was refluxed for 30 min, cooled, extracted with 100 mL ether, washed with saturated NaHCO$_3$ solution (50 mL) and brine (50 mL), dried (MgSO$_4$), and evaporated giving an oily solid. Chromatography on alumina (silica can also be used) and elution with CH$_2$Cl$_2$-petroleum ether (1:10 to 1:5) gave 635 mg (56%) of G as a yellow solid, $[\alpha]_{578}^{20} -3480°$ (c=0.015, CH$_2$Cl$_2$).

$^1$H NMR (200 MHz, CDCl$_3$) δ: 7.99 (2, 2H), 7.93 (d, J=8.2 Hz, 2H), 7.69 (d, J=8.2 Hz, 2H), 7.21 (an AB quartet, J=8.6 Hz, 4H), 7.13 (an AB quartet, J=8.0 Hz, 4H), 6.45 (dt, J=5.5, 1.8 Hz, 2H), 5.82 (dt, J=5.5, 1.9 Hz, 2H), 1.91 (dt, J=23.8, 1.7 Hz, 2H), 1.03 (dt, J=23.6, 1.7-2.0 Hz, 2H).

IR (KBr, cm$^{-1}$): 3033(m), 2923(w), 1609(w), 1385(m), 1321(m), 1254(m), 1196(w), 1160(w), 953(m), 839(vs), 775(m), 697(s), 675(m), 637(m), 566(s), 504(m), 403(w).

EXAMPLE 11

M-(−)-J (150 mg, $[\alpha]_{589} = -3480°$) was dissolved under argon in 10 mL dry THF in a 100 mL round-bottomed flask, the solution was cooled to −78° C., and 1 mL 1.6M t-butyllithium was added. The deep brown mixture was stirred at 0° C. for 90 min, cooled to −78° C., and then 105 mg CoBr$_2$.DME complex was quickly added against an argon stream. The solution was stirred at room temperature for 2 h and then cooled to −78°. Another 120 mg CoBr$_2$.DME was then added. The mixture was stirred at room temperature for 7 h. It was then quenched at 0° C. with a solution of 0.5 mL conc. HCl in 5 mL water. After stirring 2 min, 300 mg ferric chloride hexahydrate (Fisher) was added, and the mixture was stirred overnight. The deep red almost transparent solution was diluted with THF, filtered through celite, and the celite pad was washed with moist acetone. The filtrate was evaporated and the residue washed with ether (3×50 mL, the washings being discarded). The solid was dissolved in acetone-water and after 600 mg NH$_4$PF$_6$ in acetone (5 mL) was added, the solution was concentrated and the precipitate filtered. Washing this precipitate with much water (100 mL) and ether, and drying at 0.005 mmHg gave 150 mg (69%) brick-red solid, $[\alpha]_{578}^{20} = -20,300°$ (c=0.0012, acetone). Purification was achieved by adding a filtered solution of this material in acetone to vigorously stirred anhydrous ether and filtering the precipitate. The optical rotation of purified material was almost the same: $[\alpha]_{578}^{20} = -20,400°$ to 20,800°.

IR (KBr, cm$^{-1}$). 3658(m) and 3585(m, water peaks), 3115(m), 3040(m), 1699(w), 1602(s), 1495(w), 1430(w), 1385(m), 1302(w), 1245(w), 1203(w), 1167(w), 841(vs), 783(m), 731(m), 680(w), 646(w), 558(vs), 472(m), 396(w).

$^1$H NMR (300 MHz, CD$_3$COCD$_3$): 8.3-61 (br m, 14H), 6.1-5.4 (br m, 2H), 5.1-3.9 (br m, 4H).

Elemental analysis: Calculated for (C$_{36}$H$_{20}$CoPF$_6$)$_n$C, 65.85; H, 3.07; Co, 8.98; P, 4.73; F, 17.38 found C, 71.24; H, 3.90; Co, 6.72; F, —; calculated for (C$_{36}$H$_{21}$CoPF$_6$) (C$_{36}$H$_{20}$CoPF$_6$)$_2$ (C$_{36}$H$_{21}$): C, 71.35; H, 3.41; Co, 7.65.

REFERENCES

1. Katz, T. J.; Slusarek, W. *J. Am. Chem. Soc.*, 101: 4259, (1979)
2. (a) Katz, T. J.; Schulman, J. *J. Am. Chem. Soc.* 86: 3169, (1964). (b) Katz, T. J.; Balogh, V.; Schulman, J. *Ibid.*, 90: 734, (1968).
3. (a) Katz, T. J.; Pesti, J. *J. Am. Chem. Soc.* 103: 346, (1982). (b) Pesti, J. Ph.D. Dissertation, Columbia University, New York, N.Y., (1981).
4. (a) Carraher Jr., C. E.; Sheats, J. E.; Pittman Jr., C. U. "Organometallic Polymers," Academic Press: New York, (1978). (b) Hagihara, N.; Sonogashira, K.; Takahashi, S. *Adv. Polym. Sci.* 41: 149, (1981).
5. Martin observed a similar effect [Martin, R. H.; Schurter, J. J. *Tetrahedron* 28: 749, (1972).
6. (a) Martin, R. H. *Tetrahedron* 20: 897, (1964). (b) Martin, R. H.; Defay, N.; Geerts-Evard, F.; Delavarenne, S. *Ibid.* 20: 1073, (1964).
7. Sudhakar, A. Ph.D. Dissertation, Columbia University, New York, N.Y. 1985.
8. Kolle, U.; Khouzami, F. *Chem. Ber.* 114: 2929, (1981).
9. See Treichel, P. M.; Johnson, J. W.; Calabrese, J. C. *J. Organomet. Chem.* 88: 215, (1975).
10. Defay, N.; Zimmermann, D.; Martin, R. H. *Tetrahedron Lett.* p. 1871 (1971).
11. Kohler, F. H. *Chem. Ber.* 107: 570, (1974).
12. B. M. Trost, *Chem. Soc. Rev.* page 141, (1982) and references cited therein.
13. Koreeda et al., *J. Org. Chem.*, 43: 1023, (1978).
14. (a) Nesmeyanov, A. N. et al. Izv. Akad. Nauk SSSR, Ser. Khim. 667, (1963). (b) Watanabe, H., Motoyama, I.; Hata, K. Bull. Chem. Soc. Jpn. 39: 790, (1966). (c) Roling, P. V.; Rausch, M. D. J. Org. Chem. 37: 729, (1972). (d) Izumi T.; Kasahara, A. Bull. Chem Soc. Jpn. 48: 1955, (1975). (e) Bednarik, L.; Gohdes, R. C.; Neuse, E. W. Transition-Met. Chem. 2: 212, (1977).
15. Metallocene polymers and their conductivities are discussed in (a) Neuse, E. W.; Rosenberg, H. Rev. Macromol. Chem., Part 1, 5, (1970). (b) Lorkowski, H.—J. Fortschr. Chem. Forsch. 9/2: 207, (1967).
16. (a) Bilow, N.; Landis, A. L.; Rosenberg, H. J. Polym. Sci., Part A-1 7: 2719, (1969). (b) Neuse, E. W.; Crossland, R. K. J. Organomet Chem. 7: 344, (1967).

What is claimed is:

1. A helicene compound having the structure:

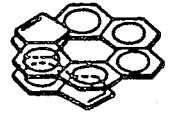

which contains seven six-membered conjugated aromatic rings capped by two five-membered rings which do not superimposed on each other.

2. A helical metallocene oligomer capped by unsaturated five-membered rings, having the structure:

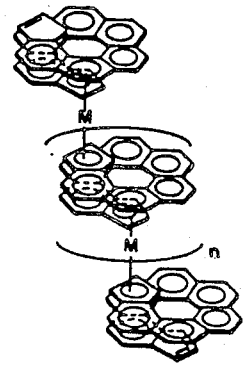

wherein M is a first row transition metal halide and n=1 to 100.

3. The oligomer of claim 2, wherein the oligomer is in optically active form.

4. The oligomer of claim 2, wherein the path of conjugation of electrons extending from one metal to the next is unbroken either by atoms that do not have available a single $\pi$ electron to continue the path of conjugation or in which the carbon skeleton does not constrain the $\pi$ electrons on adjacent atoms to almost parallel orbitals.

5. The oligomer of claim 2, wherein the halide bound to the transition metal is in the form of a hexahalophosphate.

6. The oligomer of claim 2, wherein the transition metal halide is cobalt hexafluorophosphate.

7. A method of preparing the helicene of claim 1 which comprises:

(a) contacting a compound having the structure

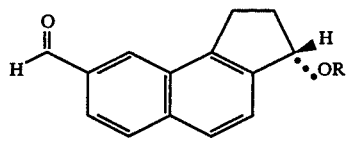

wherein R=(t-Bu)Me$_2$Si, with 1,4-bis[(C$_6$H$_5$)$_3$P$^+$CH$_2$]-2-Br—C$_6$H$_3$, under suitable conditions to form a compound having the structure:

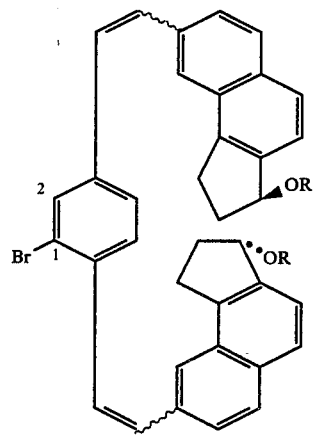

(b) subjecting the compound formed in step (a) to light energy in the presence of an acid scavenger compound which results in a photocyclization; and
(c) contacting the cyclized product of step (b) with a suitable reducing agent and an acid to form the helicene of claim 1.

8. The method of claim 7, wherein the acid scavenger of step (b) is propylene oxide.

9. A method of preparing the oligomer of claim 2 which comprises:

(a) contacting a helicene compound having the structure:

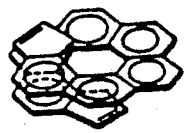

which contains seven six-membered conjugated aromatic rings capped by two five-membered rings which do not superimpose on each other, with a suitable base;

(b) contacting the product resulting from step (a) with a first row transition metal halide in a suitable solvent;
(c) contacting the product of step (b) with a suitable oxidizing agent; and
(d) contacting the product of step (c) with a hexahalophosphate salt to produce the oligomer of claim 2.

10. The method of claim 9, wherein the base of step (a) is t-butyllithium.

11. The method of claim 9, wherein the transition metal halide is cobalt dibromide.

12. The method of claim 9, wherein the oxidizing agent of step (c) is iron trichloride.

13. The method of claim 9, wherein the hexahalophosphate salt is NH$_4$PF$_6$.

14. A metallocene oligomer having the structure:

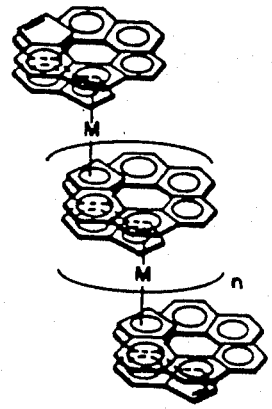

wherein M is a metal or salt thereof selected from the first row of transition elements, n=1 to 100, and wherein the path of conjugation extending from one metal to the next is unbroken.

15. An optically active oligomer of claim 14.

16. An oligomer of claim 14 which has a helical structure.

17. An oligomer of claim 15 which has a helical structure.

18. The method of claim 7 wherein the reducing agent of step (c) removes the Br group and the acid of step (c) eliminates the RO-groups to introduce two double bonds.

19. The method of claim 9 wherein the hexahalophosphate salt of step (d) substitutes for the transition metal halide.

* * * * *